(12) United States Patent
Alvarez et al.

(10) Patent No.: US 7,642,524 B1
(45) Date of Patent: Jan. 5, 2010

(54) SANITIZING APPARATUS FOR WRITING UTENSILS

(76) Inventors: Lazaro F. Alvarez, 5761 NW. 192 St., Miami, FL (US) 33015; Jorge Dierksmeier, 680 Fourth St. SE., Naples, FL (US) 34117; Howard J. Rubin, 2240 Date Palm Rd., Boca Raton, FL (US) 33432; Allan Afrow, 2917 S. Ocean Blvd., Unit 1104, Highland Beach, FL (US) 33487

(*) Notice: Subject to any disclaimer, the term of this patent is extended or adjusted under 35 U.S.C. 154(b) by 265 days.

(21) Appl. No.: 11/867,092

(22) Filed: Oct. 4, 2007

(51) Int. Cl.
*A61L 2/10* (2006.01)
*G01N 21/33* (2006.01)
*G21K 5/08* (2006.01)

(52) U.S. Cl. .............. 250/455.11; 250/492.1; 250/461.1; 422/24; 422/22; 422/186.3

(58) Field of Classification Search ........... 250/455.11, 250/461.1, 492.1; 422/24, 22, 186.3
See application file for complete search history.

(56) References Cited

U.S. PATENT DOCUMENTS 6,039,928 A * 3/2000 Roberts .................. 422/186.3
7,247,865 B2 * 7/2007 Flores et al. ............ 250/455.11
2009/0148358 A1 * 6/2009 Wind ...................... 422/186.3

* cited by examiner

Primary Examiner—Nikita Wells
(74) Attorney, Agent, or Firm—Albert Bordas, P.A.

(57) ABSTRACT

A sanitizing apparatus for writing utensils comprising a housing assembly and an ultraviolet and ozone generating assembly housed therein. The housing assembly comprises a top wall, a base and four walls. The first and second walls are perpendicularly disposed with respect to the third and fourth walls. The third and fourth walls are lateral walls. The housing assembly also comprises an angled wall that protrudes outwardly beyond the top wall and beyond the first wall defining a tray that terminates with a lip for preventing the writing utensil from falling off. A battery compartment is also housed within the housing assembly. The ultraviolet and ozone generating assembly radiates the writing utensil within the housing assembly with rays and ozone, to effectively sterilize bacteria and biological germs existing on the writing utensil. A visual indicator notifies a user when the ultraviolet and ozone generating assembly is operating.

4 Claims, 3 Drawing Sheets

SANITIZING APPARATUS FOR WRITING UTENSILS

BACKGROUND OF THE INVENTION

1. Field of the Invention

The present invention relates to sanitizing systems, and more particularly, to a sanitizing apparatus for writing utensils.

2. Description of the Related Art

Microorganisms are microscopic organisms that are too small to be seen by the human eye. Microorganisms can be bacteria, fungi, archaea or protists, but not viruses and prions, which are generally classified as non-living. Microorganisms are generally single-celled, or unicellular organisms; however, there are exceptions as some unicellular protists are visible to the average human, and some multicellular species are microscopic. Microorganisms live almost everywhere on earth, and certain microorganisms, such as pathogenic microbes, can invade other organisms and cause diseases that kill millions of people every year.

In most commercial establishments, such as banks, there are writing instruments that are often used by the general public to sign documents and the like. These writing instruments, including pens, are a haven for dangerous microorganisms. Yet at the commercial establishments, the general public typically shares them, thus spreading the dangerous microorganisms from one person to another. There is a need to sanitize writing instruments to prevent the spread of dangerous microorganisms from one person to another.

SUMMARY OF THE INVENTION

The present invention is a sanitizing apparatus for writing utensils. It comprises a housing assembly that has a top wall, a base, and first, second, third, and fourth walls. The first and second walls are perpendicularly disposed to the third and fourth walls. The third and fourth walls are lateral sidewalls that are in a parallel and spaced-apart relationship with respect to each other. The housing assembly also comprises an angled wall that is in between the third and fourth walls. The angled wall protrudes outwardly beyond the top wall a first predetermined distance and protrudes outwardly beyond the first wall a second predetermined distance. The angled wall terminates at the base and defines an elongated channeled slot through the top wall to receive at least one writing utensil. The second predetermined distance of the angled wall defines a tray that terminates with a lip, which prevents the writing utensils from falling off the tray.

The housing assembly further comprises ultraviolet and ozone generating means for radiating the writing utensils within the housing assembly with rays and ozone. This effectively sterilizes bacteria and biological germs existing within the housing assembly and on the writing utensils. The housing further comprises electronic means to notify a user when the ultraviolet and ozone generating means is operating. The electronic means comprises at least one visual indicator that illuminates to notify the user when the bacteria and biological germs are being sterilized from the writing utensils. In the preferred embodiment, the housing assembly further comprises a battery compartment for a battery power source. In an alternate embodiment, the housing assembly comprises an electrical plug to connect to an electrical outlet.

It is therefore one of the main objects of the present invention to provide a sanitizing apparatus for writing utensils to prevent the spreading of dangerous microorganisms from one person to another.

It is another object of the present invention to provide a sanitizing apparatus for writing utensils with a source of ozone by means of an ultraviolet lamp, or other ozone generator, for sterilizing microorganisms.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
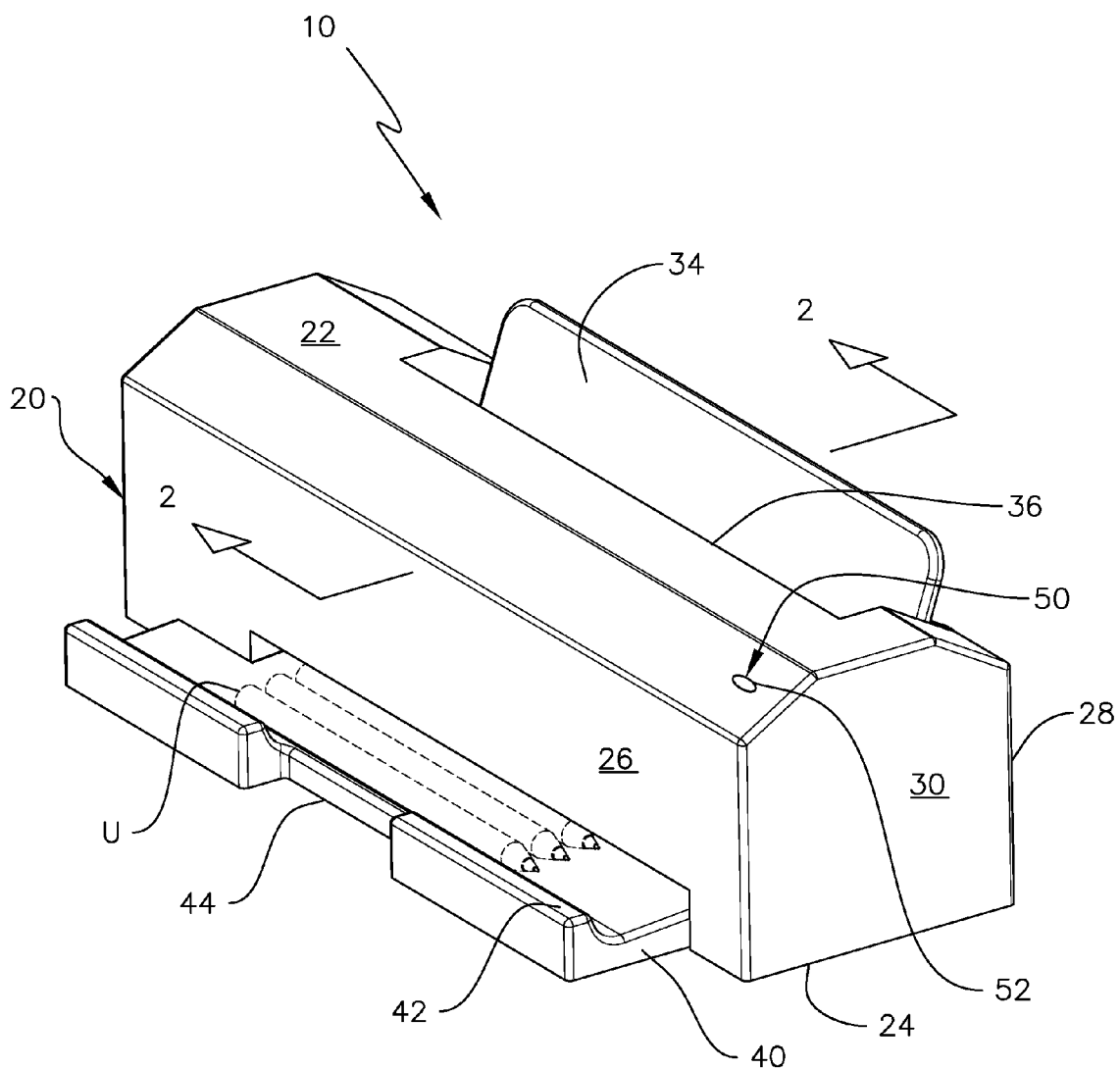
FIG. 1 represents an isometric view of the present invention, defined as a sanitizing apparatus for writing utensils.

Referring now to the drawings, the sanitizing apparatus for writing utensils is generally referred to with numeral 10. It can be observed that it basically includes housing assembly 20, and ultraviolet and ozone generating assembly 60.

Figure 2:
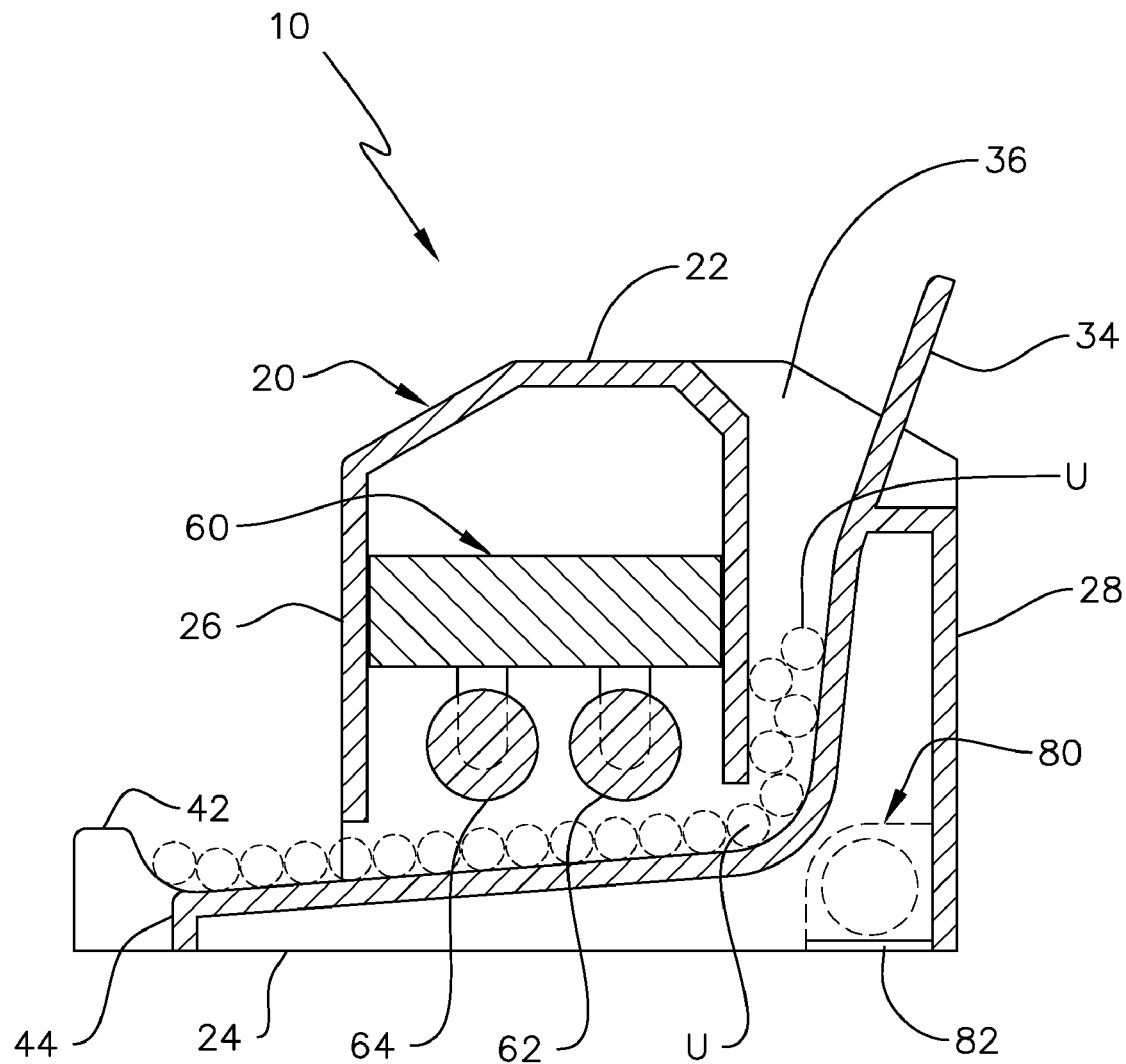
FIG. 2 is a cross-section view of the instant invention, taken along lines 2-2, seen in FIG. 1.

As seen in FIGS. 1 and 2, housing assembly 20 comprises top wall 22, base 24 and walls 26, 28, 30 and 32. Walls 26 and 28 are perpendicularly disposed with respect to walls 30 and 32. Walls 30 and 32 are lateral sidewalls that are in a parallel and spaced-apart relationship with respect to each other. Housing assembly 20 also comprises angled wall 34, which is in between walls 30 and 32. Angled wall 34 protrudes outwardly beyond top wall 22 a first predetermined distance and protrudes outwardly beyond wall 26 a second predetermined distance. The second predetermined distance portion of angled wall 34 defines tray 40. Angled wall 34 terminates at base 24.

Housing assembly 20 also comprises battery compartment 80 for a battery power source. Battery compartment 80 has door 82 that is accessible from base 24.

As seen in FIG. 2, ultraviolet and ozone generating assembly 60 is housed within housing assembly 20. Ultraviolet and ozone generating assembly 60 radiates writing utensil U within housing assembly 20 with rays and ozone, to effectively sterilize bacteria and biological germs existing within housing assembly 20 and on writing utensil U.

Ultraviolet and ozone generating assembly 60 comprises ultraviolet lamp 62 and ozone generator 64. Ultraviolet lamp 62 is known to neutralize bacteria and germs with ultraviolet rays, without detrimental side effects to the user. Ultraviolet rays produce a frequency that neutralizes bacteria and germs within housing assembly 20. Frequencies other than those known as ultraviolet can also be used if effective against bacteria and germs being suspected. As best seen in FIG. 2, ultraviolet lamp 62 and ozone generator 64 are mounted within housing assembly 20. Ozone generator 64 is affixed adjacent to ultraviolet lamp 62 and produces ozone to complement ultraviolet lamp 62.

Electronic assembly 50 is also housed within housing assembly 20. Electronic assembly 50 notifies a user when ultraviolet and ozone generating assembly 60 is operating. Electronic assembly 50 comprises visual indicator 52 that illuminates to notify the user when bacteria and biological germs are being sterilized from writing utensil U. Visual indicator 52 is preferably located on top wall 22.

In an alternate embodiment, instead of battery compartment 80, housing assembly 20 may comprise an electrical plug connected to electronic assembly 50 to connect to an electrical outlet.

Figure 3:
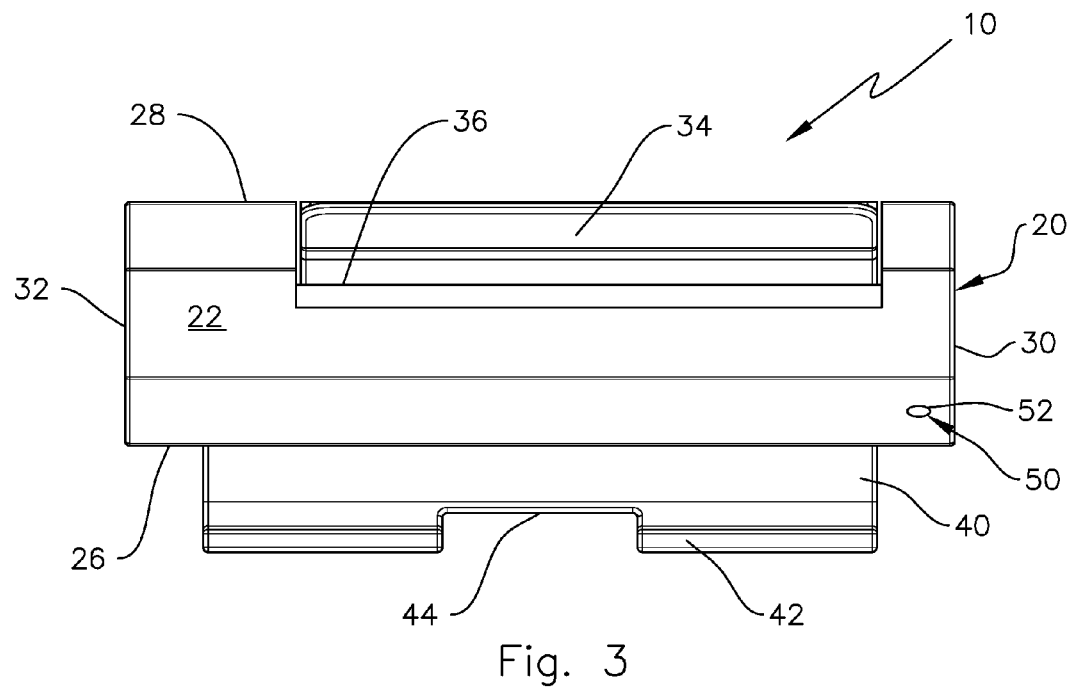
FIG. 3 shows a top plan view of the instant invention.
Figure 4:
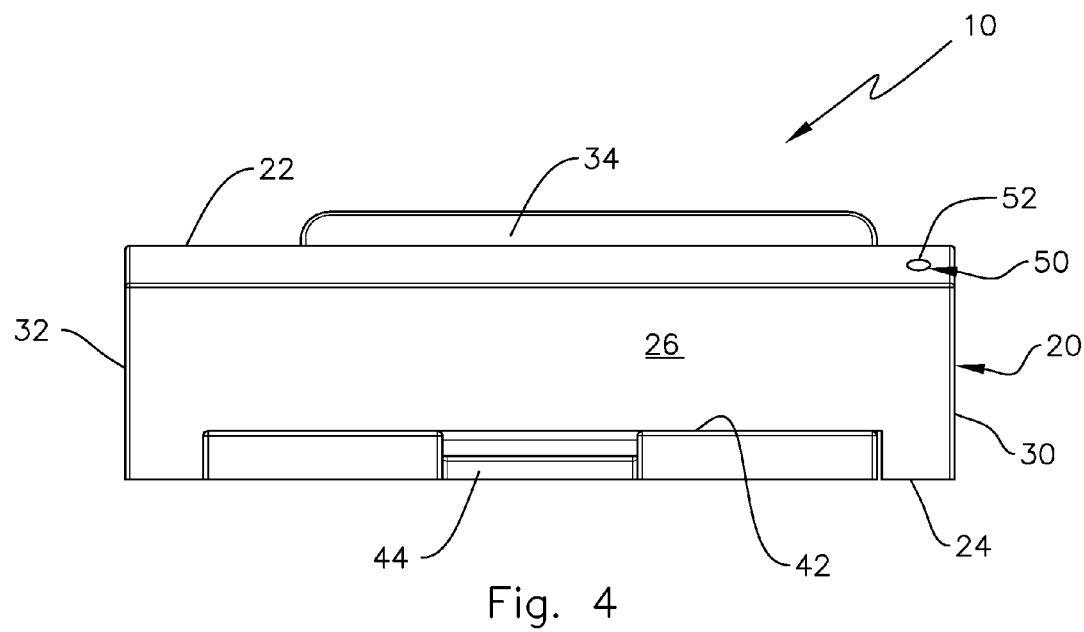
FIG. 4 is a front elevational view of the instant invention.

As seen in FIGS. 3 and 4, angled wall 34 defines elongated channeled slot 36 through top wall 22 to receive writing utensils U. It is noted that tray 40 terminates with lip 42, which prevents writing utensil U, or a plurality thereof, from falling off tray 40. Tray 40 has cutout 44 to facilitate a user in removing a sterilized writing utensil U from instant invention 10. Once the user has utilized writing utensil U, the user then inserts the used writing utensil U in through channeled slot 36 to be sterilized again. In the preferred embodiment, tray 40 alone and/or in combination with angled wall 34, contain a plurality of writing utensils U to effectively expose writing utensils U to ultraviolet lamp 62 and ozone generator 64.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A sanitizing apparatus for writing utensils, comprising a housing assembly having a top wall, a base, and first, second, third, and fourth walls, said first and second walls are perpendicularly disposed to said third and fourth walls, and said third and fourth walls are lateral sidewalls that are in a parallel and spaced-apart relationship with respect to each other, said housing assembly also comprises an angled wall, said angled wall is in between said third and fourth walls, said angled wall protrudes outwardly beyond said top wall a first predetermined distance and protrudes outwardly beyond said first wall a second predetermined distance, said angled wall terminates at said base, said angled wall defines an elongated channeled slot through said top wall to receive at least one writing utensil, said second predetermined distance of said angled wall defining a tray that terminates with a lip, said lip to prevent said at least one writing utensil from falling off said tray, said housing assembly further comprises ultraviolet and ozone generating means for radiating said at least one writing utensil within said housing assembly with rays and ozone, to effectively sterilize bacteria and biological germs existing within said housing assembly and on said at least one writing utensil.

2. The sanitizing apparatus for writing utensils set forth in claim 1, further characterized in that said housing assembly further comprises electronic means to notify a user when said ultraviolet and ozone generating means is operating, wherein said electronic means comprises at least one visual indicator that illuminates to notify said user when said bacteria and biological germs are being sterilized from said at least one writing utensil.

3. The sanitizing apparatus for writing utensils set forth in claim 2, further characterized in that said housing assembly further comprises a battery compartment for a battery power source.

4. The sanitizing apparatus for writing utensils set forth in claim 2, further characterized in that said housing assembly further comprises an electrical plug to connect to an electrical outlet.

\* \* \* \* \*